United States Patent [19]

Schlager

[11] 4,388,313
[45] Jun. 14, 1983

[54] NOVEL 3-HYDROXY-1,4-BENZODIAZEPINE-2-ONES AND PROCESS FOR THE PREPARATION THEREOF

[75] Inventor: Ludwig H. Schlager, Vienna, Austria

[73] Assignee: Gerot-Pharmazeutika Gesellschaft m.b.H., Vienna, Austria

[21] Appl. No.: 262,676

[22] Filed: May 11, 1981

Related U.S. Application Data

[63] Continuation of Ser. No. 104,998, Dec. 18, 1979, abandoned.

[30] Foreign Application Priority Data

Dec. 18, 1978 [AT] Austria ..................... 9031/78

[51] Int. Cl.³ ............... A61K 31/55; C07D 243/24
[52] U.S. Cl. .......................... 424/244; 260/239.3 D
[58] Field of Search ................. 260/239.3 D; 424/244

[56] References Cited

U.S. PATENT DOCUMENTS

| | | | |
|---|---|---|---|
| 3,296,249 | 1/1967 | Bell | 260/239.3 D |
| 3,299,053 | 1/1967 | Archer et al. | 260/239.3 D |
| 3,371,085 | 2/1968 | Reeder et al. | 260/239.3 D |
| 3,391,138 | 7/1968 | Archer et al. | 260/239.3 D |
| 3,464,978 | 9/1969 | Earley et al. | 260/239.3 D |
| 3,801,568 | 4/1974 | Nudleman et al. | 260/239.3 D |
| 4,065,451 | 12/1977 | McCaully et al. | 260/239.3 D |

OTHER PUBLICATIONS

Newger, "Organic-Chemical Drugs and Their Synonyms" (1978), pp. 533–534.
Sternbach et al., "Some Aspects of Structure Activity Relationship in Psychotropic Agents of the 1,4-benzodiazepine Series" (1966).
"Organic Reactions", vol. 5, (1949), pp. 88–89, (Wiley).
Product Catalog of EGA-Chemie (1981–1982), p. 170.
Product Catalog of Merck, (1982), p. 54.
Product Catalog of Fluka, (1982–1983), p. 164.

*Primary Examiner*—Robert T. Bond
*Attorney, Agent, or Firm*—Sughrue, Mion, Zinn, Macpeak and Seas

[57] ABSTRACT

The disclosure is directed to new 3-hydroxy-1,4-benzodiazepine-2-ones and to the process for the preparation thereof. The compounds of the invention have the structural formula

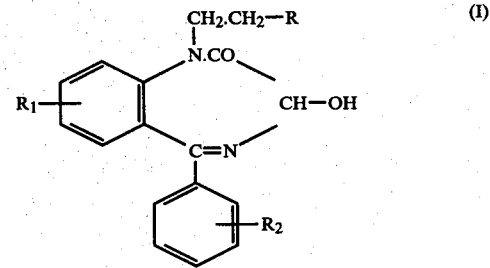

in which R is methoxy or nitrile, $R_1$ is hydrogen, halogen, trifluoromethyl or nitro and $R_2$ is hydrogen or halogen, with the proviso that R is different from methoxy, if $R_2$ is o-halogen. The compounds have marked sedative and sleep prolonging activity when evaluated in standard pharmacological procedures.

13 Claims, No Drawings

NOVEL 3-HYDROXY-1,4-BENZODIAZEPINE-2-ONES AND PROCESS FOR THE PREPARATION THEREOF

This is a continuation of application Ser. No. 104,998, filed Dec. 18, 1979 now abandoned.

SUMMARY OF INVENTION

The present invention relates to novel 3-hydroxy-1,4-benzodiazepine-2-ones of the general formula

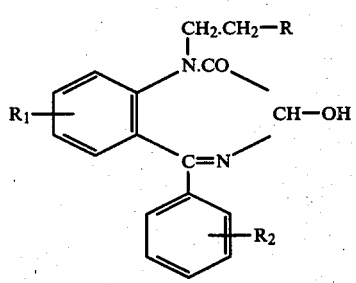

in which R is methoxy or nitrile, $R_1$ is hydrogen, halogen, trifluoromethyl or nitro and $R_2$ is hydrogen or halogen, with the proviso that R cannot be methoxy, if $R_2$ is o-halogen, and to a process for the preparation thereof.

The process of the invention comprises the selective substitution of 3-hydroxy-1,4-benzodiazepine-2-ones of the general formula

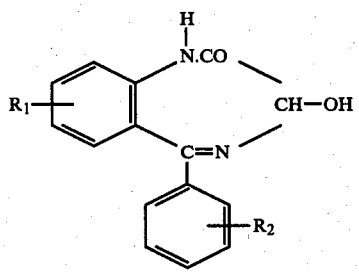

in which $R_1$ and $R_2$ are as defined above, at the NH-group, whereas the OH-group in position 3 remains unaffected.

The novel compounds of general formula (I) are pharmaceutically useful compounds which are characterized by a highly sedative and sleep prolonging activity as well as by a hexobarbital potentiating activity and show a low toxicity, which compounds may be used also as intermediate products for preparing new pharmaceuticals.

DETAILED DESCRIPTION OF THE INVENTION

Compounds of general formula (I), in which $R=OCH_3$ or CN, have not yet been described. Derivatives of formula (I), in which R has another meaning, are obtained usually by paths via the 4-oxide substituted in position 1, the Polonovsky-rearrangement thereof to give the 3-acyloxy derivative and subsequent saponification (German Offenlegungsschrift No. 2 237 211, Arzneim.Forsch. 25, 720 (1975)).

Compounds of general formula (II) are known since 1962. Nevertheless the possibility of a selective substitution at the NH-group hardly has been used up to now.

By the process of the invention it is possible to obtain from easily available compounds, such as e.g. oxazepam, lorazepam etc. (see Austrian Pat. No. 309 436) in a one-step reaction new drugs to induce sleep.

According to the process of the invention 3-hydroxy-1,4-benzodiazepin-2-ones of general formula (II) or the alkali metal salts thereof are reacted, if desired, with use of basic additives and/or with addition of phase transfer catalysts, such as quaternary ammonium or phosphonium salts or crown ethers and optionally alkali metal iodides, with compounds of the general formula

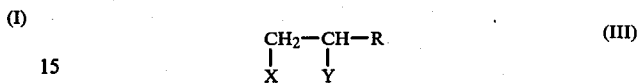

in which R is as defined above; X is a reactive radical, such as a halogen atom or a sulfonyloxy group and Y is hydrogen or, if $R=CN$, X and Y may form a double bond.

Suitable examples of compounds of general formula (III) are e.g. 2-methoxyethylchloride, 2-methoxyethylbromide or acrylonitrile as well as 3-chloropropionitrile or 3-bromopropionitrile.

The alkali metal salts of the starting products of general formula (II), which also have not been described before, may be obtained easily e.g. by reaction of these compounds with one equivalent of potassium-tert.butylate in anhydrous solvents, such as dimethylformamide or dioxane. In such a reaction first the starting product is dissolved and then the potassium salt thereof is precipitated or the potassium salt thereof may be obtained by precipitation with ethers.

In an attempt to react the alkali metal salts of the products of formula (II) thus obtained with a compound of the formula $X.CH_2CH_2-O-CH_3$, in which X is as defined above, two isomers are obtained, where $R_2$ is ortho-halogen, the isomers do not correspond with the structure of (I) ($R=OCH_3$). The same isomers are also obtained by the usually performed Polonovsky reaction via the N-oxide in hydrolysing the 1-(2-methoxyethyl)-3-acetoxy-5-(o-halogen-phenyl) derivatives.

Therefore, it is surprising that by the process of the invention new compounds of the formula (I), in which $R=OCH_3$, are obtained in a simple manner and in good yields from alkali metal salts of compounds of formula (II), in which $R_2$ is different from ortho-halogen, by reaction with a compound of the formula $XCH_2CH_2-O-CH_3$.

Furthermore, also the possibility of the selective cyanoethylation of compounds of formula (II) at the amide-nitrogen (position 1) is surprising. For instance acetanilide, which corresponds to the present structure, reacts with acrylonitrile according to experience only at 90° to 100° C., whereas the reaction thereof with secondary alcohols occurs already at room temperature or even at a lower temperature (Org. Reactions 5, 88, 89 (1949)). According to the process of the invention the reaction at the amide-nitrogen of the compounds of formula (II) commences readily at room temperature without a simultaneous substitution at the OH-group, although acrylonitrile is available in great excess as a reaction medium.

The substitution of the $-CH_2CH_2-R$ group at the amide-nitrogen may be proved by the signals of the $>CH-OH$-coupling in the n.m.r. spectra of the obtained derivatives and by the esterification of the OH-group which remained free.

The following examples illustrate the invention without limiting it thereto.

EXAMPLE 1

1 g of triethylbenzylammoniumchloride ("Teba") was added to a suspension of 10 g of 7-chloro-3-hydroxy-5-(2'-fluorophenyl)-1,3-dihydro-2H-1,4-benzodiazepine-2-one in 50 ml acrylonitrile. Then 8 drops of a 40% methanolic solution of benzyltrimethyl ammoniumhydroxide ("Triton B") were added with stirring. After stirring for 8 hours at room temperature the reaction mixture was left over night at 4° C. Then the precipitate was filtered, washed with acetone and crystallized from ethanol. The obtained 1-(2-cyanoethyl)-7-chloro-3-hydroxy-5-(2'-fluorophenyl)-1,3-dihydro-2H-1,4-benzodiazepine-2-one had a melting point of 190° to 193° C.

Without addition of Teba also the disubstituted 1-(2-cyanoethyl)-7-chloro-3-(2-cyanoethoxy)-5-(2'-fluorophenyl)-1,3-dihydro-2H-1,4-benzodiazepine-2-one was formed, which melted after recrystallization from acetonitrile at 204° to 207° C.

For distinguishing the mono- and disubstituted products from the starting material on thin layer chromatography Kieselgel 60 F 254 and as the liquid phase a mixture of benzene/dioxan/glacial acetic acid (90:25:4 parts by volume) were found suitable.

EXAMPLE 2

1 g of Teba and 8 drops of a 40% methanolic solution of Triton B were added to a suspension of 10 g of 7-chloro-3-hydroxy-5-(2'-chlorophenyl)-1,3-dihydro-2H-1,4-benzodiazepine-2-one ("Lorazepam") in 50 ml of acrylonitrile and the mixture was stirred for 24 hours at room temperature. Then the reaction mixture was cooled to 4° C., the precipitate was filtered and recrystallized from ethyl acetate. 1-(2-Cyanoethyl)-7-chloro-3-hydroxy-5-(2'-chlorophenyl)-1,3-dihydro-2H-1,4-benzodiazepine-2-one, m.p. 198° to 202° C., was obtained. Without addition of Teba also the disubstituted 1-(2-cyanoethyl)-7-chloro-3-(2-cyanoethoxy)-5-(2'-chlorophenyl)-1,3-dihydro-2H-1,4-benzodiazepine-2-one, m.p. 210° to 213° C. (from acetonitrile), is obtained.

EXAMPLE 3

68 g of the potassium salt of 7-chloro-3-hydroxy-5-phenyl-1,3-dihydro-2H-1,4-benzodiazepine-2-one ("Oxazepam") were suspended in 340 ml of 2-methoxyethyl-chloride and the suspension was heated for 20 hours to 50° C. after addition of Teba, tricaprylmethylammoniumchloride (Aliquat) and sodium iodide (each 6 g) and then heated for 15 hours to 40° C. The reaction mixture was evaporated in vacuo, the oily residue obtained was dissolved in CHCl$_3$ and shaken several times with water. The chloroform solution was dried with Na$_2$SO$_4$, filtered, evaporated and the residue was taken up into CCl$_4$. Thereby the substance crystallizes. After recrystallization from isopropanol and ethyl acetate the 1-(2-methoxyethyl)-7-chloro-3-hydroxy-5-phenyl-1,3-dihydro-2H-1,4-benzodiazepine-2-one was obtained as a colorless powder, melting point 160° to 161° C.

The potassium salt used as a starting material was obtained by heating a mixture of 60 g of Oxazepam and 24,9 g of potassium tert.butylate in 600 ml of absolute dioxan to 75° C. with stirring for one hour. First dissolution occured, then a thick precipitate was formed which was filtered from the mixture cooled over night, washed with isopropylether and dried in vacuo, melting point 192° to 197° C. (dec.).

EXAMPLE 4

3 ml of a 40% methanolic solution of Triton B was added dropwise to a suspension of 20 g of Oxazepam in 240 ml of acrylonitrile with stirring. Then the mixture was heated for one hour to 50° C. resulting in an orange colored solution. After standing over night the reaction was completed. The solution was concentrated in vacuo and upon cooling the concentrate a precipitate was obtained, which was recrystallized from CHCl$_3$. The precipitate melted at 192° to 194° C. and was determined to be 1-(2-cyanoethyl)-7-chloro-3-hydroxy-5-phenyl-1,3-dihydro-2H-1,4-benzodiazepine-2-one.

If the reaction mixture was heated for 2 hours to 50° C. also the disubstituted 1-(2-cyanoethyl)-7-chloro-3-(2-cyanoethoxy)-5-phenyl-1,3-dihydro-2H-1,4-benzodiazepine-2-one was formed, which is practically insoluble in CHCl$_3$. After recrystallization from acetonitrile the compound melted at 215° to 218° C.

EXAMPLE 5

0,1 g of Teba and 1 ml of triethylamine were added to a suspension of 2 g of Lorazepam in 20 ml of acrylonitrile and then the suspension was heated with stirring to 50° C. A yellowish solution resulted, from which gradually a precipitate was formed. After 3 hours the mixture was concentrated in vacuo and the concentrate was allowed to crystallize over night at a temperature of 4° C. The precipitate was filtered and recrystallized from ethyl acetate. It is identical with the monosubstitution product obtained according to Example 2 (melting point 198° to 202° C.).

The following new compounds were also obtained using the procedures of the above examples:

1-(cyanoethyl)-7-nitro-3-hydroxy-5-phenyl-1,3-dihydro-2H-1,4-benzodiazepine-2-one, m.p. 185° to 188° C.;

1-(2-cyanoethyl)-7-nitro-3-hydroxy-5-(2'-chlorophenyl)-1,3-dihydro-2H-1,4-benzodiazepine-2-one, m.p. 191° to 194° C.;

1-(2-cyanoethyl)-7-nitro-3-hydroxy-5-(2'-fluorophenyl)-1,3-dihydro-2H-1,4-benzodiazepine-2-one, m.p. 183° to 186° C.

What is claimed is:

1. A 3-Hydroxy-1,4-benzodiazepine-2-one of the formula

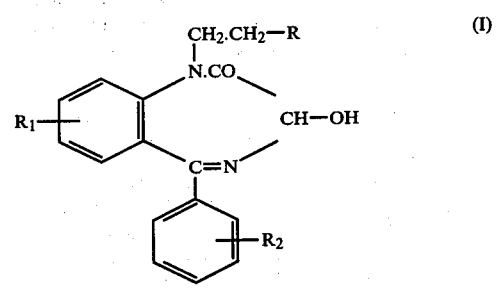

in which R is CN, R$_1$ is hydrogen, halogen, trifluoromethyl or nitro and R$_2$ is hydrogen or halogen.

2. 1-(2-Cyanoethyl)-7-chloro-3-hydroxy-5-(2'-fluorophenyl)-1,3-dihydro-2H-1,4-benzodiazepine-2-one according to claim 1.

3. 1-(2-Cyanoethyl)-7-chloro-3-hydroxy-5-(2'-chlorophenyl)-1,3-dihydro-2H-1,4-benzodiazepine-2-one according to claim 1.

4. 1-(2-Cyanoethyl)-7-chloro-3-hydroxy-5-phenyl-1,3-dihydro-2H-1,4-benzodiazepine-2-one according to claim 1.

5. 1-(2-Cyanoethyl)-7-nitro-3-hydroxy-5-phenyl-1,3-dihydro-2H-1,4-benzodiazepine-2-one according to claim 1.

6. 1-(2-Cyanoethyl)-7-nitro-3-hydroxy-5-(2'-chlorophenyl)-1,3-dihydro-2H-1,4-benzodiazepine-2-one according to claim 1.

7. 1-(2-Cyanoethyl)-7-nitro-3-hydroxy-5-(2'-fluorophenyl)-1,3-dihydro-2H-1,4-benzodiazepine-2-one according to claim 1.

8. A process for preparing a compound of formula (I) as defined in claim 1, which comprises reacting a 3-hydroxy-1,4-benzodiazepine-2-one of the general formula

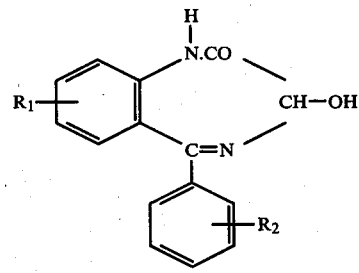

in which $R_1$ and $R_2$ are as defined in claim 1, or the alkali metal salts thereof, with a compound of the general formula

 (III)

in which X is a reactive radical and Y is hydrogen and X and Y may form a double bond.

9. The process of claim 8, in which the process is conducted in the presence of a basic additive and/or a phase transfer catalyst.

10. The process of claim 9, wherein the phase catalyst is a quaternary ammonium salt, a quaternary phosphonium salt or a crown ether.

11. The process of claim 8, wherein the process is conducted using its compound of the formula (III) or an inert solvent as a reaction medium.

12. A sedative composition comprising an amount effective to produce sedation of a compound of claim 1, 2, 3, 4, 5, 6 or 7, together with a pharmaceutically acceptable carrier or diluent.

13. A pharmaceutically active sedative composition comprising a therapeutically effective amount of 1-(cyanoethyl)-7-nitro-3-hydroxy-5-phenyl-1,3-dihydro-2H-1,4-benzodiazepine-2-one together with a material selected from the group consisting of a pharmaceutically acceptable carrier or diluent.

* * * * *